(12) United States Patent
Gliner et al.

(10) Patent No.: US 11,904,109 B2
(45) Date of Patent: Feb. 20, 2024

(54) CATHETER INTRODUCER

(71) Applicant: Biosense Webster (Israel) Ltd., Yokneam (IL)

(72) Inventors: Vadim Gliner, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 371 days.

(21) Appl. No.: 17/086,156

(22) Filed: Oct. 30, 2020

(65) Prior Publication Data

US 2022/0134053 A1 May 5, 2022

(51) Int. Cl.
*A61B 17/00* (2006.01)
*A61M 25/01* (2006.01)
*A61B 90/00* (2016.01)

(52) U.S. Cl.
CPC ............. *A61M 25/01* (2013.01); *A61B 90/04* (2016.02); *A61B 2017/00778* (2013.01)

(58) Field of Classification Search
CPC .............. A61M 25/01; A61M 25/0662; A61M 2025/0681; A61M 39/00; A61M 39/32; A61M 2039/1027; A61B 17/3415; A61B 17/3462; A61B 17/3468; A61B 2017/347; A61B 17/12022; A61B 2017/1205; A61F 2/9525; A61F 2/95
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |

(Continued)

FOREIGN PATENT DOCUMENTS

| | | |
|---|---|---|
| WO | WO 1996/005768 | 2/1996 |
| WO | 2021079236 A1 | 4/2021 |

OTHER PUBLICATIONS

Extended European Search Report dated Mar. 17, 2022, from corresponding European Application No. 21205651.9.

*Primary Examiner* — Dianne Dornbusch

(74) *Attorney, Agent, or Firm* — Troutman Pepper Hamilton Sanders LLP

(57) ABSTRACT

In one embodiment, a catheter introducer for compressing a distal end assembly of a catheter for insertion into a sheath includes a compression conduit having a truncated conical-form cavity, and including a distal and proximal opening, the proximal opening being configured to receive the distal end assembly, the cavity tapering from the proximal to the distal opening so that successive portions of the distal end assembly are compressed as the catheter is advanced distally, a distal connector connected to the distal opening, and configured to be reversibly coupled to the sheath and provide passage for the compressed portions of the distal end assembly into the sheath, and a proximal retainer disposed adjacent to the proximal opening and including opposing surfaces to at least partially prevent compression of portions of the distal end assembly while more distally disposed portions of the distal end assembly are compressed in the compression conduit.

14 Claims, 6 Drawing Sheets

(56) References Cited

U.S. PATENT DOCUMENTS

| | | |
|---|---|---|
| 2002/0065455 A1 | 5/2002 | Ben-Haim et al. |
| 2002/0165537 A1 | 11/2002 | Kelley et al. |
| 2003/0120150 A1 | 6/2003 | Govari |
| 2004/0068178 A1 | 4/2004 | Govari |
| 2010/0160946 A1* | 6/2010 | Mirizzi ............ A61B 17/12181 606/191 |
| 2012/0296313 A1 | 11/2012 | Andreacchi et al. |
| 2013/0172883 A1 | 7/2013 | Lopes et al. |
| 2014/0296706 A1 | 10/2014 | Chronos et al. |
| 2015/0289929 A1 | 10/2015 | Toth et al. |
| 2016/0346106 A1* | 12/2016 | Hacker et al. |
| 2018/0303414 A1* | 10/2018 | Toth et al. |
| 2021/0113812 A1* | 4/2021 | Lopez et al. |

\* cited by examiner

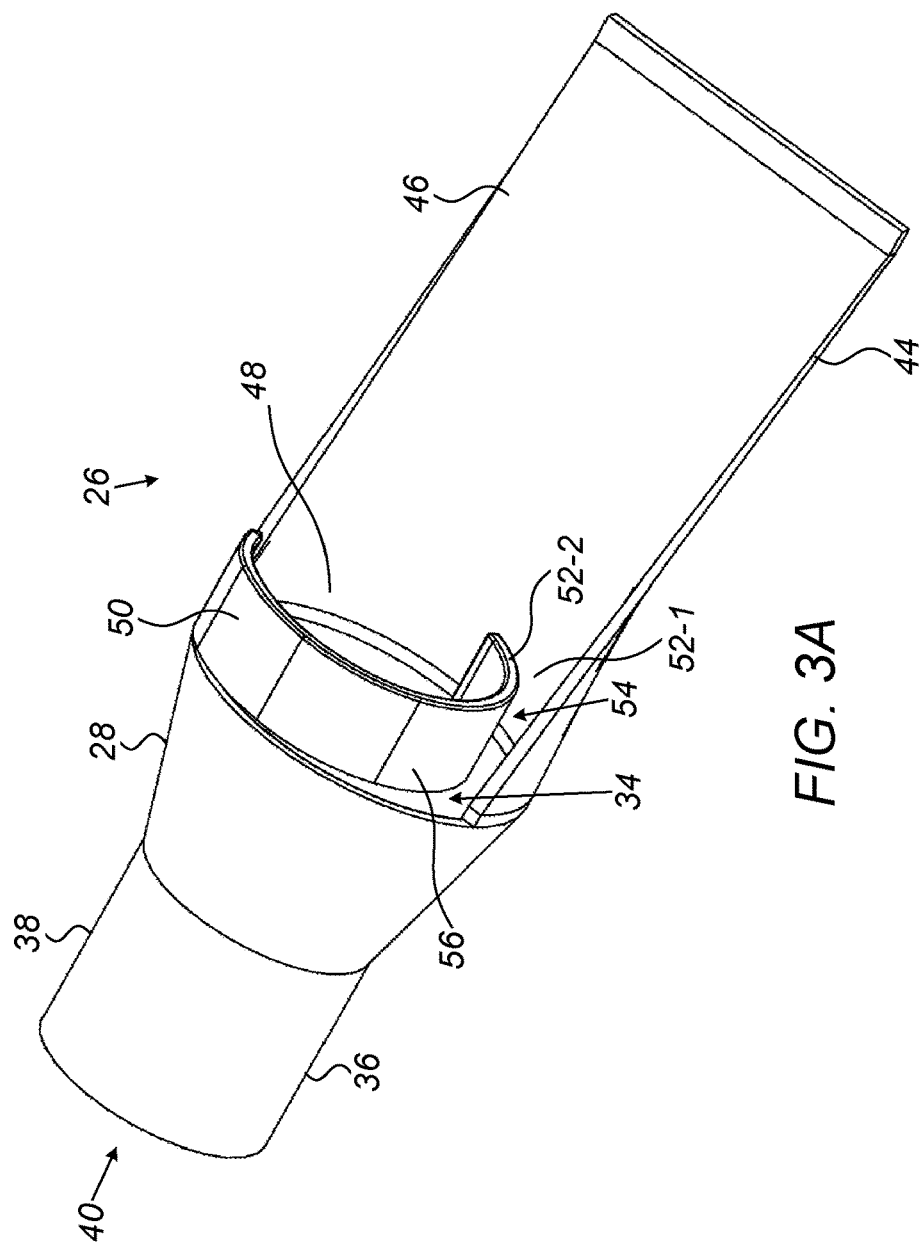
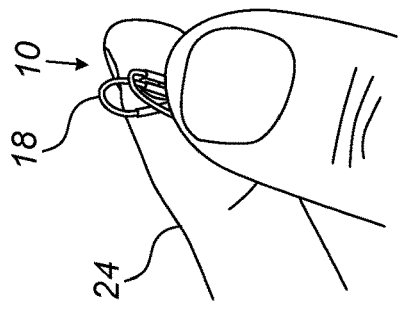
FIG. 2A
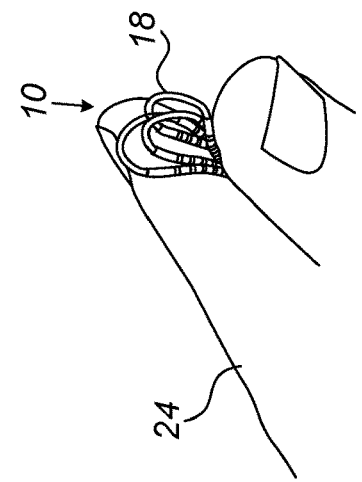
FIG. 2B
FIG. 3A

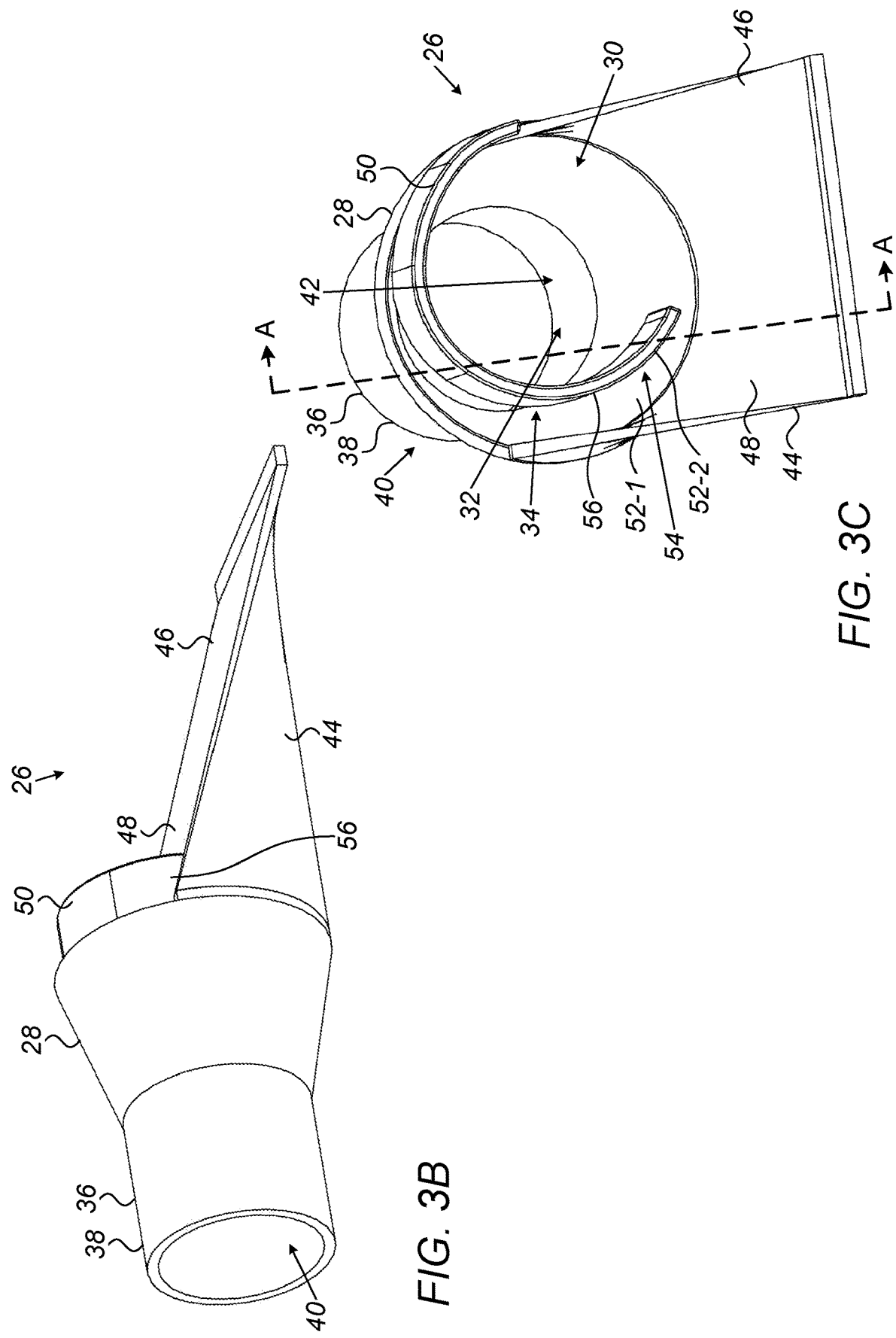

CATHETER INTRODUCER

FIELD OF THE INVENTION

The present invention relates to medical systems, and in particular, but not exclusively to, introducing a catheter into a sheath.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied between the catheter electrode(s) of the ablating catheter and an indifferent electrode (which may be one of the catheter electrodes), and current flows through the media between the electrodes, i.e., blood and tissue. The distribution of current may depend on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. In some applications, irreversible electroporation may be performed to ablate the tissue.

The catheter may include a distal end assembly, which is inserted in a folded configuration, through a sheath previously inserted through the blood vessels of the patient, and only after the catheter exits the sheath does the distal end assembly regain its intended functional shape. By containing the distal end assembly in a folded configuration, the sheath also serves to minimize vascular trauma on its way to the target location.

US Patent Publication 2018/0303414 of Toth, et al., describes systems, devices, and methods for performing precise treatment, mapping, and/or testing of tissues.

US Patent Publication 2015/0289929 of Toth, et al., describes a system for controlled sympathectomy procedures, a system for controlled micro ablation procedures, methods for performing a controlled surgical procedure, a system for performing controlled surgical procedures in a minimally invasive manner, and systems and methods for accessing target tissues as part of a neuromodulation procedure from within a lumen.

US Patent Publication 2014/0296706 of Chronos, et al., describes a device for characterizing a luminal dimension, such as the aortic annulus including a balloon or basket with sensing and transmitting elements for assessing the two- or three-dimensional shape of lumens using a guide wire and catheter. Sheath introducer devices were developed for percutaneous delivery of bioprosthetic valves during various percutaneous procedures, such as TAVI. A marker needle dispenser for pre-marking anatomical features that are either desirable to target or desirable to avoid has been developed. The needle contains a central passage or lumen for loading marker and spacer material. These are characterized by specific spacing, color, shape or diagnostic imaging criteria to facilitate passage through and placement within the vasculature. Hemostatic stents or balloons are used to prevent bleeding and facilitate closure at sites for entry of catheters or introducer sheaths into luminal structures, especially for procedures such as TAVI through the subclavian artery.

US Patent Publication 2013/0172883 of Lopes, et al., describes systems, methods, and devices allowing intravascular or percutaneous mapping, orientation or ablation, or combinations thereof in bodily cavities or lumens. A device includes a plurality of elongate members which are moveable between an unexpanded configuration, a bent or coiled stack configuration and an expanded or fanned configuration. The elongate members form a stack arrangement in the unexpanded configuration to fit through a catheter sheath. The elongate members follow respective arcuate or curvilinear paths as advanced from the sheath into the bent or coiled stack configuration, adopting volute, scroll or rho shapes, and may be nested. The elongated members are fanned or radially spaced circumferentially with respect to one another into the expanded or fanned configuration. Transducers carried by elongate members may sense various physiological characteristics of or proximate tissue, for instance temperature, and/or may apply energy to or proximate tissue, for example to perform ablation. The device is retractable.

SUMMARY

There is provided in accordance with an embodiment of the present disclosure, a catheter introducer apparatus for compressing a distal end assembly of a catheter for insertion into a sheath, which is configured to be inserted into a vessel of a living subject, the apparatus including a compression conduit having a truncated conical-form cavity, and including a distal opening and a proximal opening, the proximal opening being configured to receive the distal end assembly of the catheter therein, the cavity tapering from the proximal opening to the distal opening so that successive respective portions of the distal end assembly are compressed as the catheter is advanced distally in the cavity, a distal connector connected to the distal opening of the compression conduit, and configured to be reversibly coupled to the sheath and to provide passage for the compressed portions of the distal end assembly from the compression conduit into the sheath, and a proximal retainer disposed adjacent to the proximal opening and including two opposing surfaces defining a gap through which at least part of the distal end assembly is inserted, the opposing surfaces being configured to at least partially prevent compression of portions of the distal end assembly while more distally disposed portions of the distal end assembly are being compressed in the compression conduit.

Further in accordance with an embodiment of the present disclosure the distal end assembly of the catheter includes a grid-shaped distal end assembly including a plurality of splines.

Still further in accordance with an embodiment of the present disclosure the distal connector includes a tube having a distal opening and a proximal opening, the proximal opening of the tube being connected to the distal opening of the compression conduit and the distal opening of the tube being configured to provide an exit to the sheath when the sheath is coupled to the distal connector.

Additionally, in accordance with an embodiment of the present disclosure, the apparatus includes an entry ramp connected to the proximal opening of the compression conduit, and including a surface on which to rest the catheter as the catheter is inserted into the compression conduit.

Moreover, in accordance with an embodiment of the present disclosure the surface of the entry ramp includes a distal curved portion connected to the proximal opening of the compression conduit so that there is smooth transition between the surface of the entry ramp and the cavity of the compression conduit.

Further in accordance with an embodiment of the present disclosure the opposing surfaces of the proximal retainer include a first curved opposing surface and a second curved opposing surface, the first curved opposing surface being included in the distal curved portion of the entry ramp, the proximal retainer including a curved element including the second curved opposing surface.

Still further in accordance with an embodiment of the present disclosure the curved element of the proximal retainer is included in a curved open loop which extends over part of the distal curved portion of the entry ramp.

Additionally, in accordance with an embodiment of the present disclosure the opposing surfaces of the proximal retainer include a first curved opposing surface and a second curved opposing surface.

Moreover, in accordance with an embodiment of the present disclosure the proximal retainer includes a curved open loop including a curved element including the second curved opposing surface.

There is also provided in accordance with another embodiment of the present disclosure, a medical system including a sheath configured to be inserted into a vessel of a living subject, a catheter configured to be inserted into the sheath and including a distal end assembly, and a catheter introducer apparatus configured to compress the distal end assembly of the catheter for insertion into the sheath, and including a compression conduit having a truncated conical-form cavity, and including a distal opening and a proximal opening, the proximal opening being configured to receive the distal end assembly of the catheter therein, the cavity tapering from the proximal opening to the distal opening so that successive respective portions of the distal end assembly are compressed as the catheter is advanced distally in the cavity, a distal connector connected to the distal opening of the compression conduit, and configured to be reversibly coupled to the sheath and to provide passage for the compressed portions of the distal end assembly from the compression conduit into the sheath, and a proximal retainer disposed adjacent to the proximal opening and including two opposing surfaces defining a gap through which at least part of the distal end assembly is inserted, the opposing surfaces being configured to at least partially prevent compression of portions of the distal end assembly while more distally disposed portions of the distal end assembly are being compressed in the compression conduit.

Further in accordance with an embodiment of the present disclosure the distal end assembly of the catheter includes a grid-shaped distal end assembly including a plurality of splines.

Still further in accordance with an embodiment of the present disclosure the distal connector includes a tube having a distal opening and a proximal opening, the proximal opening of the tube being connected to the distal opening of the compression conduit and the distal opening of the tube being configured to provide an exit to the sheath when the sheath is coupled to the distal connector.

Additionally, in accordance with an embodiment of the present disclosure, the system includes an entry ramp connected to the proximal opening of the compression conduit, and including a surface on which to rest the catheter as the catheter is inserted into the compression conduit.

Moreover, in accordance with an embodiment of the present disclosure the surface of the entry ramp includes a distal curved portion connected to the proximal opening of the compression conduit so that there is smooth transition between the surface of the entry ramp and the cavity of the compression conduit.

Further in accordance with an embodiment of the present disclosure the opposing surfaces of the proximal retainer include a first curved opposing surface and a second curved opposing surface, the first curved opposing surface being included in the distal curved portion of the entry ramp, the proximal retainer including a curved element including the second curved opposing surface.

Still further in accordance with an embodiment of the present disclosure the curved element of the proximal retainer is included in a curved open loop which extends over part of the distal curved portion of the entry ramp.

Additionally, in accordance with an embodiment of the present disclosure the opposing surfaces of the proximal retainer include a first curved opposing surface and a second curved opposing surface.

Moreover, in accordance with an embodiment of the present disclosure the proximal retainer includes a curved open loop including a curved element including the second curved opposing surface.

There is also provided in accordance with still another embodiment of the present disclosure, a catheter introducer method for compressing a distal end assembly of a catheter for insertion into a sheath, which is configured to be inserted into a vessel of a living subject, the method including inserting and distally advancing the distal end assembly into a proximal opening of a compression conduit having a truncated conical-form cavity, which tapers from the proximal opening to a distal opening so that successive respective portions of the distal end assembly are compressed as the catheter is advanced distally in the cavity, reversibly coupling the sheath to a distal connector connected to the distal opening of the compression conduit, advancing the distal end assembly into the sheath via the distal connector, which provides passage for the compressed portions of the distal end assembly from the compression conduit into the sheath.

Further in accordance with an embodiment of the present disclosure, the method includes at least partially preventing compression of portions of the distal end assembly while more distally disposed portions of the distal end assembly are being compressed in the compression conduit using a proximal retainer disposed adjacent to the proximal opening and including two opposing surfaces defining a gap through which at least part of the distal end assembly is inserted.

BRIEF DESCRIPTION OF THE DRAWINGS

The present invention will be understood from the following detailed description, taken in conjunction with the drawings in which:

FIGS. 2A-B are schematic views of the catheter of FIG. 1 being manually compressed for insertion into the sheath of FIG. 1;

FIGS. 3A-C are schematic views of catheter introducer apparatus constructed and operative in accordance with an embodiment of the present invention;

DESCRIPTION OF EXAMPLE EMBODIMENTS

Overview

Figure 1:
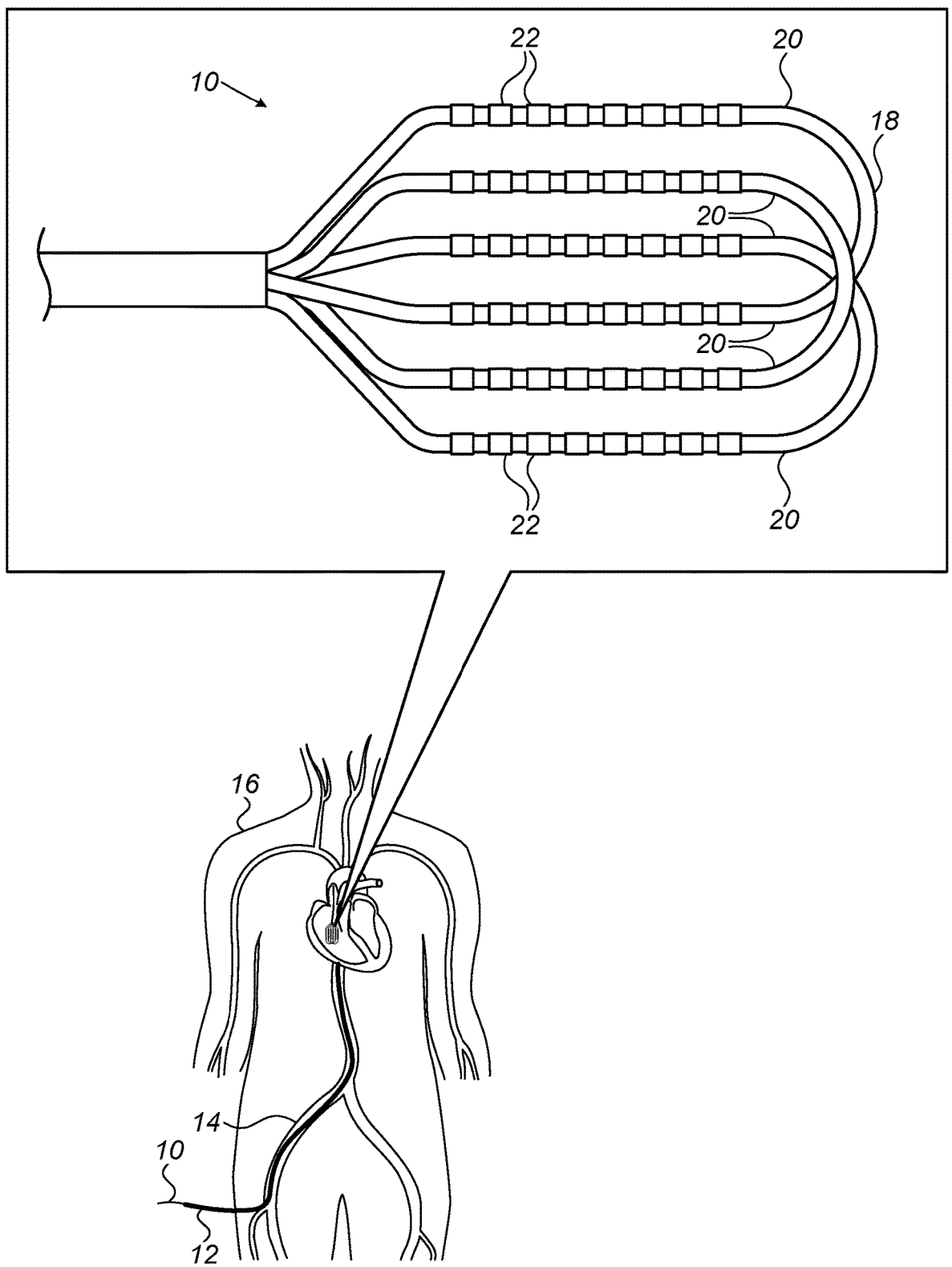
FIG. 1 is a schematic view of a catheter inserted into a sheath in a vessel of a living subject constructed and operative in accordance with an embodiment of the present invention.

Catheters with grid-shaped distal end assemblies include multiple electrodes and are very useful for performing diagnostic and mapping functions. The grid may comprise an arrangement (e.g., planar arrangement) of electrodes disposed on multiple splines which are joined together at their distal and proximal ends.

In use, the grid-shaped distal end assembly of the catheter is inserted in a folded configuration, through a sheath previously inserted (or to be inserted) through the blood vessels of the patient, and only after the catheter exits the sheath does the distal end assembly regain its intended functional shape, e.g., the grid shape. By containing the distal end assembly in a folded configuration, the sheath also serves to minimize vascular trauma on its way to the target location.

In order to be inserted into the sheath, the grid needs to be compressed to fit in a sheath having an inner diameter of between 3 to 10 mm. When the grid is squeezed manually (e.g., with fingers), the distal end of the grid tends to spread out making it very difficult to collapse the grid sufficiently for insertion into the sheath.

Embodiments of the present invention solve the above problem by providing a catheter introducer apparatus for compressing a catheter and facilitating insertion of the catheter into a sheath. The introducer includes an entry ramp on which the grid-shaped distal end assembly of the catheter is placed. The ramp may curve inwards as it moves from the proximal end of the ramp to the distal end of the ramp.

The ramp terminates at a compression conduit including a truncated conical-form cavity. The cavity has a distal and proximal opening. The proximal opening receives the distal end assembly of the catheter therein. The cavity tapers from the proximal to the distal opening so that successive respective portions of the distal end assembly are compressed as the catheter is advanced distally in the cavity.

In some embodiments, the surface of the entry ramp includes a distal curved portion connected to the proximal opening of the compression conduit so that there is smooth transition between the surface of the entry ramp and the cavity of the compression conduit.

A distal connector (e.g., a tube) is connected to the distal opening of the compression conduit, and the sheath is reversibly coupled to distal connector, e.g., to the outside of the distal connector. The interior of the distal connector provides passage for the compressed portions of the distal end assembly from the compression conduit into the sheath.

In some cases, while the distal end assembly is being compressed in the compression conduit, more proximal portions of the distal end assembly may also be compressed leading to the proximal ends of the splines of the distal end assembly colliding and leading to the distal end assembly not collapsing correctly. Therefore, in some embodiments, the introducer includes a proximal retainer, which is adjacent to the proximal opening, and at least partially prevents the more proximal portions of the distal end assembly compressing while the more distal portions of the distal end assembly are being compressed.

In some embodiments, the proximal retainer has two opposing surfaces (e.g., a lower surface opposing an upper surface) defining a gap through which at least part of the width of the distal end assembly is inserted. The opposing surfaces at least partially prevent compression of portions of the distal end assembly while more distally disposed portions of the distal end assembly are being compressed in the compression conduit. In some embodiments, the proximal retainer allows splines on one side of the distal end assembly to fold over splines on the other side of the distal end assembly so that distal end assembly may be compressed correctly. For example, splines on the right side of the distal end assembly may fold over splines on the left side of the distal end assembly as the left side is supported in the gap of the proximal retainer.

In some embodiments, the opposing surfaces of the proximal retainer include a first curved opposing surface (e.g., a lower curved surface) and a second curved opposing surface (e.g., an upper curved surface). In some embodiments, the first curved opposing surface is included in the distal curved portion of the entry ramp and the proximal retainer includes a curved element including the second curved opposing surface.

In some embodiments, the curved element of the proximal retainer is included in a curved open loop which extends over part of the distal curved portion of the entry ramp so that the second curved surface of the curved open loop is disposed above the first curved surface, which is included in the entry ramp.

System Description

Reference is now made to FIG. 1, which is a schematic view of a catheter 10 inserted into a sheath 12 in a vessel 14 of a living subject 16 constructed and operative in accordance with an embodiment of the present invention. The sheath 12 is configured to be inserted into the vessel 14 of the living subject 16. The catheter 10 is configured to be inserted into the sheath 12. The catheter 10 comprises a distal end assembly 18. In some embodiments, the distal end assembly 18 of the catheter 10 includes a grid-shaped distal end assembly 18 (e.g., a planar distal end assembly 18 comprising a plurality of splines 20 substantially defining a plane). Each spline may include one or more electrodes 22 (only some labeled for the sake of simplicity). The splines 20 are described as "substantially defining a plane" in that if any of the splines 20 are translated by up to 2 mm, the same plane would intersect at least 70% of the length of each of the splines 20. In some embodiments, at least 50% of the length of the splines 20 may be parallel within an error of plus or minus 30 degrees.

Reference is now made to FIGS. 2A-B, which are schematic views of the catheter 10 of FIG. 1 being manually compressed for insertion into the sheath 12 of FIG. 1. In order to be inserted into the sheath 12, the distal end assembly 18 needs to be compressed to fit in the sheath 12, which may have an inner diameter of between 3 to 10 mm, by way of example only. When the distal end assembly 18 is squeezed manually (e.g., with fingers 24), the distal end of the grid-shaped distal end assembly 18 tends to spread out making it very difficult to collapse the grid-shaped distal end assembly 18 sufficiently for insertion into the sheath 12 as shown in FIGS. 2A and 2B.

Figure 4:
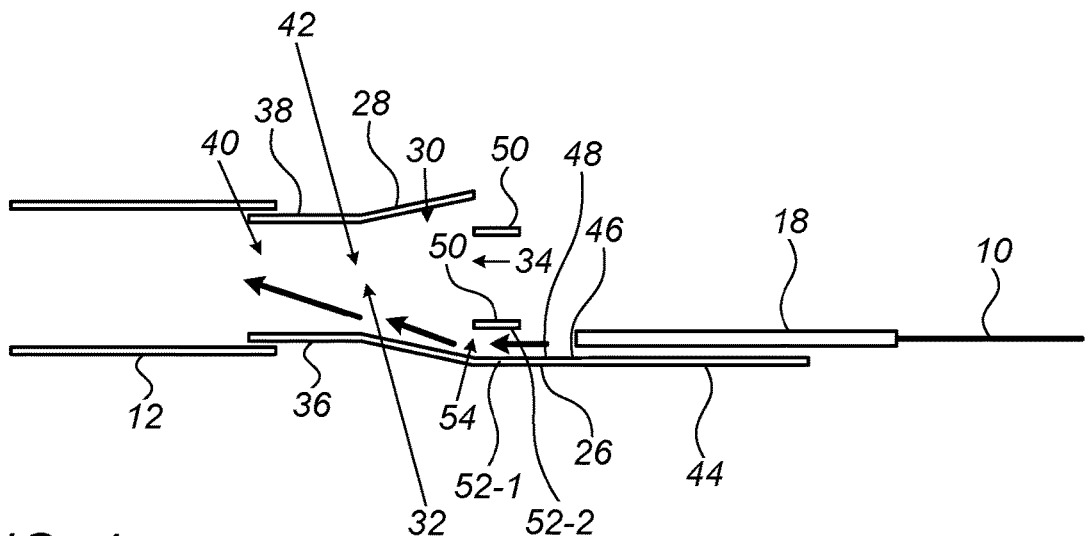
FIG. 4 is a cross-section view of the catheter introducer apparatus of FIG. 3C through line A:A illustrating introduction of the catheter into the sheath of FIG. 1.

Reference is now made to FIGS. 3A-C, which are schematic views of a catheter introducer apparatus 26 constructed and operative in accordance with an embodiment of the present invention. Reference is also made to FIG. 4, which is a cross-section view of the catheter introducer apparatus 26 of FIG. 3C through line A:A illustrating introduction of the catheter 10 into the sheath 12 of FIG. 1. It should be noted that due to the different views shown in FIGS. 3A-C, 4, some of the reference numerals may only appear in one or more, but not all, of the reference figures.

The catheter introducer apparatus 26 is configured to compress the distal end assembly 18 of the catheter 10 for insertion into the sheath 12.

The catheter introducer apparatus 26 comprises a compression conduit 28 having a truncated conical-form cavity 30, and including a distal opening 32 and a proximal opening 34. The proximal opening 34 is configured to receive the distal end assembly 18 of the catheter 10 therein. The cavity 30 tapers from the proximal opening 34 to the distal opening 32 so that successive respective portions of the distal end assembly 18 are compressed as the catheter 10 is advanced distally in the cavity 30. The inner diameter or width of the proximal opening 34 may be any suitable size, for example in the range of 10 to 40 mm, and may be sized so that half of the perimeter (e.g., circumference) of the proximal opening 34 is equal to about the width of the distal end assembly 18. The width and thickness of the distal end assembly 18 are defined as dimensions measured perpendicular to the directional of elongation of the catheter 10, with the width being a larger dimension than the thickness.

The inner diameter or width of the distal opening 32 may have any suitable size, for example in the range of 3 to 10 mm. The truncated conical-form cavity 30 may have any suitable length (taking the quickest route from the distal opening 32 to the proximal opening 34), for example, between 1 to 5 cm.

The catheter introducer apparatus 26 comprises a distal connector 36 connected to the distal opening 32 of the compression conduit 28, and configured to be reversibly coupled to the sheath 12 (FIG. 4) and to provide passage for the compressed portions of the distal end assembly 18 from the compression conduit 28 into the sheath 12. In some embodiments the distal connector may be combined with the compression conduit 28 so that the outer surface of the compression conduit 28 connects with the sheath 12 and the distal opening 32 of the conduit 28 exits directly into the sheath 12.

In some embodiments, the distal connector 36 comprises a tube 38 having a distal opening 40 and a proximal opening 42. The proximal opening 42 of the tube 38 is connected to the distal opening 32 of the compression conduit 28 and the distal opening 40 of the tube 38 is configured to provide an exit for the compressed catheter 10 to the sheath 12 when the sheath 12 is coupled to the distal connector 36. The tube 38 may have any suitable inner diameter, for example, about equal to the inner diameter of the distal opening 32 of the compression conduit 28. The tube 38 may have any suitable outer diameter, for example, about equal to the inner diameter of the sheath 12. The tube 38 may have any suitable length, for example in the range between 2 to 30 mm or longer.

The catheter introducer apparatus 26 may comprise an entry ramp 44 connected to the proximal opening 34 of the compression conduit 28. The entry ramp 44 includes a surface 46 on which to rest the catheter 10 as the catheter 10 is inserted into the compression conduit 28. The entry ramp 44 may be flat and/or curved. In some embodiments, the entry ramp 44 starts off flat at its proximal end and curves towards its distal end as shown in FIGS. 3A-C. In some embodiments, the surface 46 of the entry ramp 44 includes a distal curved portion 48 connected to the proximal opening 34 of the compression conduit 28 so that there is smooth transition between the surface 46 of the entry ramp 44 and the truncated conical-form cavity 30 of the compression conduit 28. The proximal end of the entry ramp 44 may have any suitable width, for example, a width about the same as the width of the distal end assembly 18. The distal end of the entry ramp 44 has a curved width (measured along the curve of the distal curved portion 48) equal to about the width of the distal end assembly 18. The entry ramp 44 may have any suitable length, for example, in the range of 2 to 40 mm. In some embodiments, the entry ramp 44 is not included, or could be part of the truncated conical-form cavity 30 of the compression conduit 28.

The catheter introducer apparatus 26 comprises a proximal retainer 50 disposed adjacent to the proximal opening 34 and includes two opposing surfaces 52 (including a lower surface 52-1 and an upper surface 52-1) defining a gap 54 through which at least part of the distal end assembly 18 is inserted. The opposing surfaces 52 are configured to at least partially prevent compression (and/or collision) of portions of the distal end assembly 18 while more distally disposed portions of the distal end assembly 18 are being compressed in the compression conduit 28. The terms "lower" and "upper" are defined with respect to normal use of the catheter introducer apparatus 26 by the operator of the catheter introducer apparatus 26. However, the catheter introducer apparatus 26 may be used in any suitable orientation. The gap 54 may have any suitable measurement measured between the opposing surfaces 52 depending on the thickness and construction of the distal end assembly 18. In some embodiments, the gap 54 may be in the range of 1 to 5 mm. The width of the opposing surfaces 52 may have any suitable value. In some embodiments, the width of the opposing surfaces 52 is between one-quarter and one-half, e.g., one-third, of the width of the distal end assembly 18. In general, the opposing surfaces 52 are wide enough across the width of the distal end assembly 18 to sufficiently prevent portions of distal end assembly 18 from compressing (and/or colliding) while more distally disposed portions of the distal end assembly 18 are being compressed in the compression conduit 28. More or less width of the opposing surfaces 52 may be needed depending on the thickness of the distal end assembly 18 and design and the distance between the opposing surfaces 52.

In some embodiments, the opposing surfaces 52 of the proximal retainer 50 include a first curved opposing surface 52-1 (e.g., a lower curved surface) and a second curved opposing surface 52-2 (e.g., an upper curved surface). In some embodiments, the first curved opposing surface 52-1 is comprised in the distal curved portion 48 of the entry ramp 44 and the proximal retainer 50 comprises a curved element 56 comprising the second curved opposing surface 52-2.

In some embodiments, the curved element 56 of the proximal retainer 50 is comprised in a curved open loop (as shown in FIGS. 3A-C) which extends over part of the distal curved portion 48 of the entry ramp 44 so that the second curved surface 52-2 of the curved open loop is disposed above the first curved surface 52-1, which is comprised in the entry ramp 44.

In some embodiments, the proximal retainer 50 may be disposed at least partially internally to the compression conduit 28.

Figure 5:
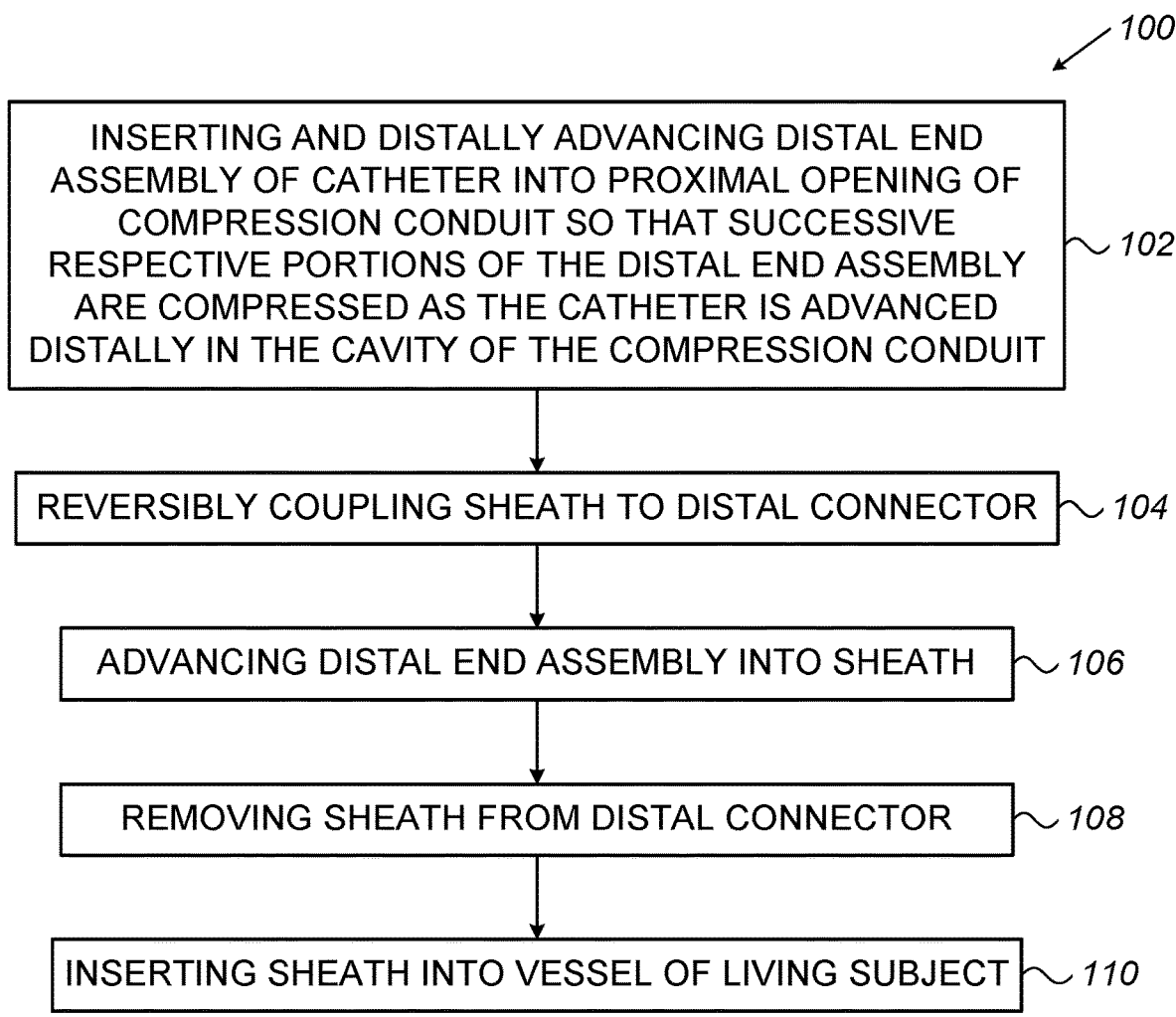
FIG. 5 is a flowchart including steps in a method of introducing the catheter into the sheath of FIG. 1.

Reference is now made to FIG. 5, which is a flowchart 100 including steps in a method of introducing the catheter 10 into the sheath 12 of FIG. 1. Reference is also made to FIG. 4.

The method includes inserting and distally advancing (block 102) the distal end assembly 18 into the proximal opening 34 of the compression conduit 28 so that successive respective portions of the distal end assembly 18 are compressed as the catheter 10 is advanced distally in the truncated conical-form cavity 30 while at least partially preventing compression of portions of the distal end assembly 18 while more distally disposed portions of the distal end assembly 18 are being compressed in the compression conduit 28 using the proximal retainer 50.

Figure 6A:
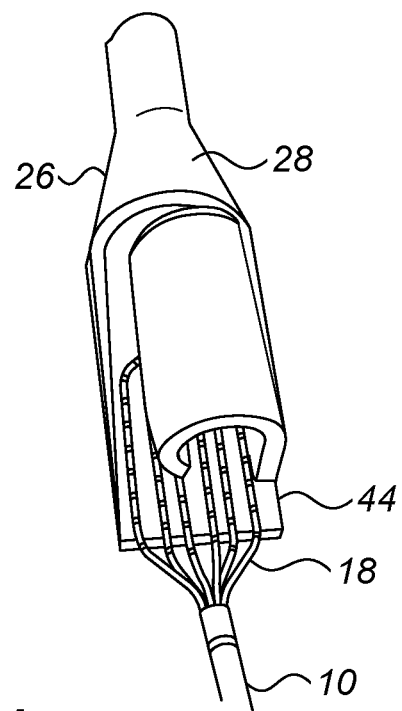
FIGS. 6A-D are schematic views illustrating compression of a distal end assembly of the catheter of FIG. 1.
Figure 6B:
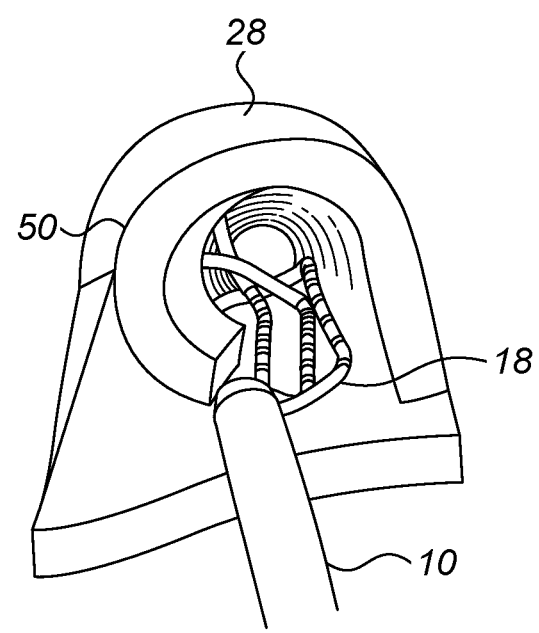
Figure 6C:
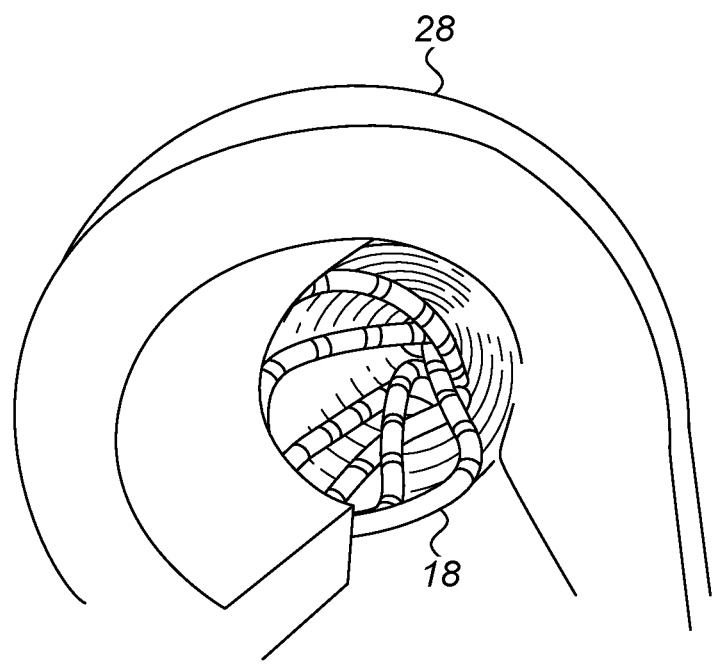
Figure 6D:
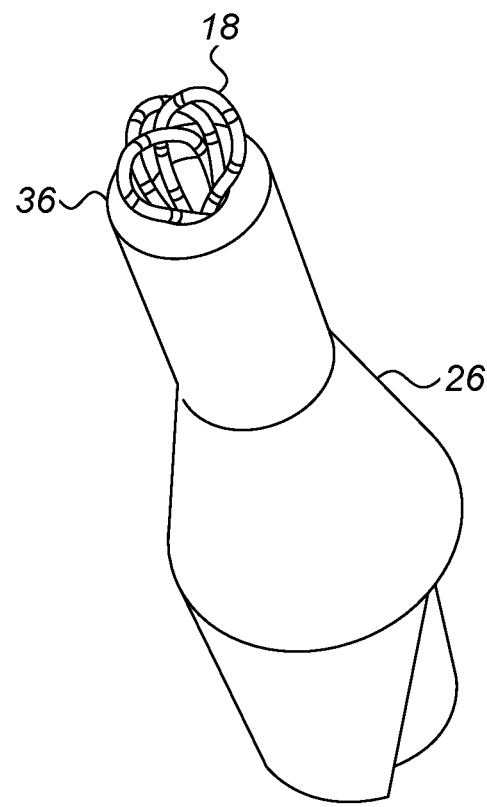

Reference is now made to FIGS. 6A-D, which are schematic views illustrating compression of the distal end assembly 18 of the catheter 10 of FIG. 1. FIG. 6A shows the distal end assembly 18 resting on the entry ramp 44 prior to insertion into the compression conduit 28. FIG. 6B shows the distal end of the distal end assembly 18 entering the compression conduit 28 and being compressed while the proximal end of the distal end assembly 18 is partially prevented from compressing using the proximal retainer 50. FIG. 6C shows the distal end assembly 18 mostly in the compression conduit 28 and being compressed. FIG. 6D shows a distal portion of the distal end assembly 18 exiting the distal connector 36 of the catheter introducer apparatus 26 in a compressed state.

Reference is again made to FIG. 5. Reference is also made to FIG. 4. The method also includes reversibly coupling (block 104) the sheath 12 to the distal connector 36, and advancing (block 106) the distal end assembly 18 into the sheath 12 via the distal connector 36. The method also includes removing (block 108) the sheath 12 from the distal connector 36 and inserting (block 110) the sheath 12 into the vessel 14 (FIG. 1) of the living subject 16 (FIG. 1). The above steps may be performed in any suitable order.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A catheter introducer apparatus for compressing a distal end assembly of a catheter for insertion into a sheath, which is configured to be inserted into a vessel of a living subject, the apparatus comprising:
    a compression conduit having a truncated conical-form cavity, and including a distal opening and a proximal opening, the proximal opening being configured to receive the distal end assembly of the catheter therein, the cavity tapering from the proximal opening to the distal opening so that successive respective portions of the distal end assembly are compressed as the catheter is advanced distally in the cavity;
    a distal connector connected to the distal opening of the compression conduit, and configured to be reversibly coupled to the sheath and to provide passage for the compressed portions of the distal end assembly from the compression conduit into the sheath; and
    a proximal retainer disposed adjacent to the proximal opening and including two opposing surfaces defining a gap through which at least part of the distal end assembly is inserted, the opposing surfaces being configured to at least partially prevent compression of portions of the distal end assembly while more distally disposed portions of the distal end assembly are being compressed in the compression conduit, the opposing surfaces of the proximal retainer including a first curved opposing surface and a second curved opposing surface, and the proximal retainer including a curved open loop comprising a curved element including the second curved opposing surface.

2. The apparatus according to claim 1, wherein the distal end assembly of the catheter includes a grid-shaped distal end assembly comprising a plurality of splines.

3. The apparatus according to claim 1, wherein the distal connector comprises a tube having a distal opening and a proximal opening, the proximal opening of the tube being connected to the distal opening of the compression conduit and the distal opening of the tube being configured to provide an exit to the sheath when the sheath is coupled to the distal connector.

4. The apparatus according to claim 1, further comprising an entry ramp connected to the proximal opening of the compression conduit, and including a surface on which to rest the catheter as the catheter is inserted into the compression conduit.

5. The apparatus according to claim 4, wherein the surface of the entry ramp includes a distal curved portion connected to the proximal opening of the compression conduit so that there is smooth transition between the surface of the entry ramp and the cavity of the compression conduit.

6. The apparatus according to claim 5, the first curved opposing surface being comprised in the distal curved portion of the entry ramp.

7. A catheter introducer apparatus for compressing a distal end assembly of a catheter for insertion into a sheath, which is configured to be inserted into a vessel of a living subject, the apparatus comprising:
- a compression conduit having a truncated conical-form cavity, and including a distal opening and a proximal opening, the proximal opening being configured to receive the distal end assembly of the catheter therein, the cavity tapering from the proximal opening to the distal opening so that successive respective portions of the distal end assembly are compressed as the catheter is advanced distally in the cavity;
- a distal connector connected to the distal opening of the compression conduit, and configured to be reversibly coupled to the sheath and to provide passage for the compressed portions of the distal end assembly from the compression conduit into the sheath;
- a proximal retainer disposed adjacent to the proximal opening and including two opposing surfaces defining a gap through which at least part of the distal end assembly is inserted, the opposing surfaces being configured to at least partially prevent compression of portions of the distal end assembly while more distally disposed portions of the distal end assembly are being compressed in the compression conduit; and
- an entry ramp connected to the proximal opening of the compression conduit, and including a surface on which to rest the catheter as the catheter is inserted into the compression conduit,
- the surface of the entry ramp including a distal curved portion connected to the proximal opening of the compression conduit so that there is smooth transition between the surface of the entry ramp and the cavity of the compression conduit,
- the opposing surfaces of the proximal retainer including a first curved opposing surface and a second curved opposing surface, the first curved opposing surface being comprised in the distal curved portion of the entry ramp, the proximal retainer comprising a curved element comprising the second curved opposing surface,
- the curved element of the proximal retainer being comprised in a curved open loop which extends over part of the distal curved portion of the entry ramp.

8. A medical system comprising:
- a sheath configured to be inserted into a vessel of a living subject;
- a catheter configured to be inserted into the sheath and comprising a distal end assembly; and
- a catheter introducer apparatus configured to compress the distal end assembly of the catheter for insertion into the sheath, and comprising:
  - a compression conduit having a truncated conical-form cavity, and including a distal opening and a proximal opening, the proximal opening being configured to receive the distal end assembly of the catheter therein, the cavity tapering from the proximal opening to the distal opening so that successive respective portions of the distal end assembly are compressed as the catheter is advanced distally in the cavity;
  - a distal connector connected to the distal opening of the compression conduit, and configured to be reversibly coupled to the sheath and to provide passage for the compressed portions of the distal end assembly from the compression conduit into the sheath; and
  - a proximal retainer disposed adjacent to the proximal opening and including two opposing surfaces defining a gap through which at least part of the distal end assembly is inserted, the opposing surfaces being configured to at least partially prevent compression of portions of the distal end assembly while more distally disposed portions of the distal end assembly are being compressed in the compression conduit, the opposing surfaces of the proximal retainer including a first curved opposing surface and a second curved opposing surface, and the proximal retainer including a curved open loop comprising a curved element including the second curved opposing surface.

9. The system according to claim 8, wherein the distal end assembly of the catheter includes a grid-shaped distal end assembly comprising a plurality of splines.

10. The system according to claim 8, wherein the distal connector comprises a tube having a distal opening and a proximal opening, the proximal opening of the tube being connected to the distal opening of the compression conduit and the distal opening of the tube being configured to provide an exit to the sheath when the sheath is coupled to the distal connector.

11. The system according to claim 8, further comprising an entry ramp connected to the proximal opening of the compression conduit, and including a surface on which to rest the catheter as the catheter is inserted into the compression conduit.

12. The system according to claim 11, wherein the surface of the entry ramp includes a distal curved portion connected to the proximal opening of the compression conduit so that there is smooth transition between the surface of the entry ramp and the cavity of the compression conduit.

13. The system according to claim 12, the first curved opposing surface being comprised in the distal curved portion of the entry ramp.

14. The system according to claim 13, wherein the curved open loop extends over part of the distal curved portion of the entry ramp.

* * * * *